United States Patent
Bublewitz et al.

(10) Patent No.: US 6,523,992 B1
(45) Date of Patent: Feb. 25, 2003

(54) DEVICE FOR MIXING TWO PASTY SUBSTANCES, PARTICULARLY FOR MIXING A DENTAL IMPRESSION SUBSTANCE WITH CATALYST SUBSTANCE

(75) Inventors: Alexander Bublewitz, Herborn (DE); Matthias Suchan, Hachenburg (DE)

(73) Assignee: Kettenbach GmbH & Co. KG, Eschenburg (DE)

(*) Notice: Subject to any disclaimer, the term of this patent is extended or adjusted under 35 U.S.C. 154(b) by 0 days.

(21) Appl. No.: 09/709,499

(22) Filed: Nov. 13, 2000

(30) Foreign Application Priority Data

Nov. 12, 1999 (DE) .......................................... 199 54 515
Nov. 30, 1999 (DE) .......................................... 199 57 600
Sep. 9, 2000 (DE) .......................................... 100 44 762

(51) Int. Cl.[7] .............................. B01F 5/04; B01F 7/00
(52) U.S. Cl. ................. 366/172.1; 366/312; 366/326.1; 366/329.1; 222/145.6
(58) Field of Search .................. 366/172.1, 172.2, 366/176.1, 181.5, 312, 325.1, 325.2, 329.1, 329.2, 326.1; 222/145.5, 145.6

(56) References Cited

U.S. PATENT DOCUMENTS

| | | | | |
|---|---|---|---|---|
| 3,051,455 A | * | 8/1962 | Magester |
| 3,226,093 A | * | 12/1965 | Gugel et al. |
| 3,302,832 A | * | 2/1967 | Hardman et al. |
| 3,390,814 A | * | 7/1968 | Creighton, Jr. et al. |
| 3,570,719 A | * | 3/1971 | Schiff |
| 3,587,982 A | * | 6/1971 | Campbell |
| 3,711,067 A | * | 1/1973 | Kovacs |
| 3,767,085 A | * | 10/1973 | Cannon et al. |
| 4,107,793 A | * | 8/1978 | Wallace |
| 4,432,469 A | * | 2/1984 | Eble et al. |
| 4,471,888 A | * | 9/1984 | Herb et al. |
| 4,767,025 A | * | 8/1988 | Gebauer et al. |
| 4,934,827 A | * | 6/1990 | Taschke et al. |
| 4,951,843 A | * | 8/1990 | Paetow |
| 5,249,862 A | * | 10/1993 | Herold et al. |
| 6,244,740 B1 | * | 6/2001 | Wagner et al. |
| 6,311,871 B1 | * | 11/2001 | Binder |
| 6,352,177 B1 | * | 3/2002 | Bublewitz et al. |
| 6,394,643 B1 | * | 5/2002 | Bublewitz et al. |
| 6,443,612 B1 | * | 9/2002 | Keller |
| 2001/0005338 A1 | * | 6/2001 | Muhlbauer et al. |

FOREIGN PATENT DOCUMENTS

| | | | |
|---|---|---|---|
| DE | 2949369 | * | 6/1981 |
| DE | 4235736 | * | 3/1994 |
| DE | 29705741 | * | 9/1998 |

(List continued on next page.)

*Primary Examiner*—Charles E. Cooley
(74) *Attorney, Agent, or Firm*—Diller, Ramik & Wight (57) ABSTRACT

The device for mixing two pasty substances, particularly for mixing a dental impression substance with a catalyst substance, comprises a housing with a substantially tubular portion. At least two inlet openings (68) for the two pasty substances are arranged at the rear end of said housing, and an outlet opening for the mixed pasty substances is arranged at the front end of said housing. The housing comprises a coupling portion joining the tubular portion and having two coupling openings for connecting the housing with two outlet openings of a device for dispensing the two pasty substances. The coupling openings are connected to the inlet openings (68) via first and second channels (64,66) extending through the coupling portion. At least one mixer element is arranged within the tubular portion of the housing for mixing the two pasty substances when the substances are passing through the tubular portion of the housing. The first channel (64) or the second channel (66) or both channels (64,66) extend to at least two inlet openings (68). All inlet openings (68) are spatially separated from each other. The first channel(s) (64) is (are) separated from the second channel(s) (66).

6 Claims, 3 Drawing Sheets

FOREIGN PATENT DOCUMENTS

| | | | |
|---|---:|---|---|
| DE | 10015133 | * | 9/2001 |
| EP | 87029 | * | 8/1983 |
| EP | 603492 | * | 6/1994 |
| EP | 1072323 | * | 1/2001 |
| EP | 1110599 | * | 6/2001 |
| EP | 1149627 | * | 10/2001 |
| JP | 6-226178 | * | 8/1994 |
| JP | 8-187727 | * | 7/1996 |
| JP | 2001-207996 | * | 8/2001 |
| WO | 00/21652 | * | 4/2000 |
| WO | 01/24919 | * | 4/2001 |

* cited by examiner

DEVICE FOR MIXING TWO PASTY SUBSTANCES, PARTICULARLY FOR MIXING A DENTAL IMPRESSION SUBSTANCE WITH CATALYST SUBSTANCE

BACKGROUND OF THE INVENTION

The instant invention relates to a device for mixing two pasty substances, particularly for mixing a dental impression substance (basic substance) and a catalyst substance for initiating and/or accelerating the polymerization of the dental impression substance.

A device of the above type is mounted onto the outlet connector of a dispensing device by which, through application of pressure onto the pasty substances contained either in cartridges or in film hose packs, these substances are introduced into the mixing device and after mixing in the mixing device are issued therefrom as a mixture.

In a large number of technical uses, it is required that two pasty substances, which have been stored separate from each other, are applied in mutually mixed form. For this purpose, use is made either of dynamic or static flow mixers designed to mix the pasty substances with each other while these are flowing through the mixer housings.

A dynamic mixer is known e.g. from EP-A-0 492 412. This known device comprises a substantially tubular mixer housing with a mixer shaft arranged for rotation therein. The mixer shaft is provided with a plurality of radially projecting vane-shaped mixing elements for mixing the pasty substances with each other when the mixer shaft is driven. The pasty substances enter the mixer housing via a radial end wall at the rear end of the mixer housing. For this purpose, the end wall is provided with two inlet connectors arranged to be mounted onto the outlet connectors of a device for delivery of the pasty substances. The two inlet openings of the end wall through which the pasty substances enter the mixer housing, are arranged diametrically opposite each other and are axially oriented relative to the mixer shaft. Thus, the two sites where the pasty substances enter the mixer chamber are arranged at a considerable distance, making the mixing process more difficult.

Known from EP-A-0 885 651 is a static mixer wherein a mixer chamber includes a plurality of mixing elements behind each other and in fixed positions. The two pasty substances to be mixed enter the mixer chamber via separate inlet openings. These openings are arranged on diametrically opposite sites of the mixer housing. One of the two pasty substances is caused to reach the inlet openings for the other pasty substance along a curved channel and will then together with the other substance into the actual mixer chamber having the mixer elements arranged therein. Thus, the two pasty substances will enter the mixer chamber of the mixer housing together through the same inlet openings. This causes a danger of backward contamination, i.e. a contamination spreading in reverse flow direction, with the possible result that at least one of the two pasty substances is hardened up into the outlet connector of the dispenser device so that, from this point of time, no pasty material can be discharged from the respective film hose bag or the respective cartridge and the pasty substances still remaining in the cartridge or the film bag hose cannot be used anymore.

It is an object of the invention to provide a device for mixing two pasty substances which guarantees a largely homogeneous mixing of both substances.

SUMMARY OF THE INVENTION

According to the instant invention, the above object is achieved by a device for mixing two pasty substances, particularly for mixing a dental impression substance with a catalyst substance, comprising a housing comprising a substantially tubular portion and at least two inlet openings for the two pasty substances at the rear end of said housing, and an outlet opening for the mixed pasty substances at the front end of said housing, said housing being provided with a coupling portion joining said tubular portion and having two coupling openings formed therein for connecting the housing with two outlet openings of a device for dispensing the two pasty substances, and said coupling openings being connected to said inlet openings via first and second channels extending through said coupling portion, and at least one mixer element arranged within said tubular portion of the housing for mixing the two pasty substances when the substances are passing through the tubular portion of the housing.

According to the invention, the above device is characterized in that said first channel or said second channel or both of said channels extend to at least two inlet openings, said inlet openings are spatially separated from each other, and said first channel or said first channels are separated from said second channel or said second channels.

Thus, according to the general idea of the invention, it is provided that all of the pasty substances are introduced via separate inlet openings into the actual mixer chamber of the mixer housing. Therefore, no mutual mixing or contacting of the pasty substances will occur prior to passing these inlet openings. Further, at least one of the two inlet openings will enter the mixer chamber of the mixer housing via more than one inlet opening. Particularly, this mixer chamber is said substantially tubular portion of the mixer housing. The connection of the inlet openings to the coupling openings of the mixer housing which are preferably formed as connecting studs, is established via channels extending from the coupling openings to the inlet openings. Thus, at least one of the two channels leads from the appertaining coupling opening to a plurality of inlet openings. For this purpose, this channel can be configured to split into individual partial channels which under the aspect of flow technology are connected in parallel and terminate in the inlet openings. By way of alternative, a plurality of inlet openings can be arranged along the extension of the channel, connecting the channel with the actual mixer chamber of the mixer housing. Thus, in this case, the inlet openings are arranged in a row.

A further variant of a channel leading to more than one inlet opening resides can be realized by a distributor channel which is connected to the appertaining coupling opening and is connected via inlet openings to the actual mixer chamber of the mixer housing.

By introducing at least one of the two pasty substances into the mixer chamber at a plurality of separate sites, an improved mixing of the two pasty substances is obtained. The reason is to be seen in that the substance flow of said one pasty substance is divided among a plurality of inlet openings of the tubular portion of the housing and the mixer chamber, respectively. The improved mixing is achieved without a mutual contact of the two pasty substances occurring already prior to entry into the mixer chamber. This is advantageous if it is desired to prevent backward contamination.

According to a preferred embodiment of the invention, it is provided that one of the two channels extends to a sole inlet opening and the other channel extends to two inlet openings. Thus, the mixer chamber comprises three inlet openings altogether. Preferably, these inlet openings are distributed in a uniform configuration. This uniform distribution can be provided either in the circumferential direction or in the axial direction of the mixer chamber. Even if more than three inlet openings are provided, and irrespective of the numerical distribution of these inlet openings among the two channels, it will be of particular advantage if all of the inlet openings are distributed in a uniform configuration.

The orientation of the inlet openings relative to the actual mixer chamber, i.e. relative to the substantially tubular portion of the housing, can be substantially radial and/or substantially axial. Further, it is possible to provide both radial and axial inlet openings.

The inventive concept of introducing at least one of the two substances on a plurality of spatially separated sites of the mixer chamber can be realized both in a static and a dynamic mixer, i.e. in a mixer with stationary mixer elements as well as in a mixer with rotary mixing elements.

To prevent that a pasty substance entering the mixer chamber from its dedicated inlet opening will flow directly to the inlet opening associated to the other pasty substance, it is of advantage if baffle or deflection plates are arranged between adjacent inlet openings in the mixer chamber to thus interrupt the direct connection between adjacent inlet openings. These baffle or deflection plates interrupt at least the direct path between adjacent inlet openings. Still, under the aspect of flow technology, the adjacent inlet openings remain in connection with each other via the mixer chamber; however, this flow connection is rendered more difficulty by the arrangement of the baffle plates, thus reducing the danger that one pasty substance in the mixer chamber might reach the inlet opening for the other pasty substance. This in turn decreases the danger of backward contamination.

The number and the relative arrangement of the baffle elements is preferably equal to the number and the relative arrangement of the inlet openings. This is advantageous particularly if the baffle elements, in case of a dynamic mixer, are arranged on the mixer shaft. Notably, this identical number and arrangement of baffle elements and inlet openings has the effect that adjacent inlet openings are partitioned against each other in each rotational position of the mixer shaft. This can be obtained by fully or largely blocking the inlet openings by the baffle elements, or by means of the baffle elements arranged between two adjacent inlet openings.

The baffle elements sweep across the inlet openings at least partially. Depending on the respective application, it may be suitable to completely close the inlet openings at least for short phases. Generally, however, it is preferred that the size of the baffle elements and/or their extension in the circumferential direction is adjusted to the size of the inlet openings in such a manner that the latter will not be completely closed when the baffle elements move by the inlet openings.

In addition to the function of interrupting the direct connection between adjacent inlet openings, the baffle elements, in case of a dynamic mixer, i.e. a mixer with driven mixer shaft, are also provided to enhance the transport of the pasty substances into the mixer chamber. By providing the baffle elements with deflection faces extending obliquely relative to a radial plane of the mixer shaft, the baffle elements can be used for axially deflecting the pasty substances while these are radially flowing into the tubular portion of the housing. Suitably, in this case, each baffle element is formed as a wedge. In view of their deflection function, the baffle elements will also be referred to as baffle/deflection elements. The extension of the baffle/deflection elements in the circumferential direction should be selected such that the baffle elements can at maximum occupy the circumferential region between two inlet openings. If the baffle elements are too small in the circumferential direction, their effectiveness for enhancing the deflection of the pasty substances might be decreased.

Thus, in the above described embodiment of the inventive mixing device, the infeed of the pasty substances to be mixed is performed radially into the substantially tubular portion of the mixer housing. For this purpose, the tubular portion of the housing is provided with two inlet openings which are particularly arranged diametrically opposite each other. The streams of pasty substances introduced into the mixer by application of pressure, will within the tubular portion of the housing impinge on the baffle/deflection elements extending around the axis of the mixer shaft. These baffle/deflection elements rotate along with the rotating mixer shaft and are each formed with a deflection face extending obliquely to a radial plane of the axis. In other words, the baffle/deflection elements are provided as substantially saw-tooth-shaped wedges extending in a bent shape around the axis of the mixer shaft. The baffle/deflection elements act in the manner of a worm conveyer in a worm pump and have the effect that the onflowing pasty material is directly removed in the axial direction from the inlet openings toward the outlet opening. Thus, backward contamination is reliably prevented since the at least one baffle/deflection element will always enhance the axial transport of the pasty substances entering the tubular portion of the mixer housing via the inlet openings.

As already explained above, the baffle/deflection elements can be respectively wedge-shaped. By way of alternative to this wedge-shape, the baffle/deflection elements can be formed as a web extending helically around the axis; thus, in this embodiment, the baffle/deflection elements have the shape of a screw thread. Such surrounding webs are known from worm pumps and worm conveyers.

Preferably, the mixer shaft is provided, at the level of the inlet openings of the tubular portion of the mixer housing, with at least one scraper bar arranged at a distance from the axis of the mixer shaft and extending in parallel thereto. Thus, the scraper bar is located at an interval to the axis of the mixer shaft and extends in parallel to the shaft. Surprisingly, tests have shown that such a scraper bar and particularly two such scraper bars arranged diametrically opposite each other will improve the mixing of the two substance flows. A variant wherein a respective scraper bar is arranged between adjacent baffle/deflection elements has proven to be of particular advantage.

To lend a largely straightforward design to the dynamic mixer of the invention, the housing is at its rear end provided with an insert member oriented transverse to the axis and having two inlet connectors projecting therefrom. The insert member is arranged in a conically flared housing portion of the mixer joining the tubular housing portion and comprises the channels projecting from the inlet connector. These two channels are arranged to extend along an angled path radially into a central cylindrical receiving recess on the inner side of the insert member wherein the axis of the mixer shaft with the baffle/deflection elements is received. Thus, the cylindrical receiving recess of the insert member forms a partial region of the tubular housing portion of the mixer. The two inlet connectors of the insert member form the coupling openings and are provided to be mounted onto the outlet connectors of the dispensing or press-out device. It is also possible to design the outlet connectors for mounting onto the inlet connectors. From the inlet connectors, the two channels extend to the inlet openings provided in a number larger than three.

The baffle/deflection elements safeguard that the respective adjacent inlet openings within the plane formed by them or within said recess, will not be in direct fluid communication. Instead, in each rotational position of the mixer shaft, one of the baffle/deflection elements will be arranged at least partially in the region between two adjacent inlet openings or will substantially close the inlet openings. This effect is obtained in that the number and the relative position of the baffle/deflection elements is provided to be identical with the number and relative position of the inlet openings. Alternatively, more than one baffle/deflection element can be provided per inlet opening. Thus, the number of inlet openings is equal to the number of baffle/deflection elements, with each group comprising at least one baffle/ deflection element. The configuration of the group within itself is equal to the configuration of the inlet openings to each other. In this arrangement, the inlet openings and the baffle/deflection elements, and the groups of baffle/ deflection elements, respectively, are arranged at a uniform distribution in a region of 360°. Thus, in case of three inlet openings, these are arranged at a mutual displacement of 120°. Accordingly, also the three baffle/deflection elements or, more accurately, the three groups of baffle/deflection elements, are arranged at a mutual displacement of 120°.

Within the three groups, the baffle/deflection elements can be arranged in a uniform manner or at different mutual distances. Further, each baffle/deflection element or each group of baffle/deflection elements preferably extends beyond the circumferential extension of the largest one of the inlet openings. By the measures described above, it is accomplished that, in each rotational position of the mixer shaft, at least one baffle/deflection element will "block" the "free" path between two adjacent inlet openings. This is advantageous for the prevention of backward contamination. Additionally, the danger of such backward contamination also reduced by the immediate removal of the substances entering via the inlet openings, with the substance flows being deflected in the direction of the mixer elements arranged downstream of the baffle/deflection elements.

By the baffle/deflection elements and mixer elements arranged in different axial portions of the mixer shaft, the cylindrical housing portion receiving the mixer shaft is functionally separated into a first baffle/deflection portion as viewed in flow direction, with mutual shading of the inlet openings for preventing a mixing of the substances and thus precluding a backward contamination, and a mixing portion arranged downstream of the baffle/deflection element for mixing the substances According to a preferred embodiment of the invention, the tubular housing portion has provided therein, between the inlet openings and the radial outlet opening, with a plurality of mixing elements which in the manner of radial bars extend from the axis and which reach to an area close to the inner surface of the tubular housing portion. These mixing elements are arranged within a plurality of radial plane at a distance from the shaft and provide for a deflection of the substance flows passing through the housing. This leads to the desired mixing. The mixing effect is further intensified if these mixing elements, which due to their radial orientation prevent a direct flow between the inlet openings and the outlet openings, are arranged along a larger angular region, e.g. 90°. This can be realized in that adjacent mixing elements are connected to each other by a circumferential segment. This provision results in mixing elements formed as quarter-circles, it being advantageous if these quarter-circles, when viewed in the circumferential direction, have their central portions arranged at a larger distance from the inner surface of the tubular portion of the housing than the ends of the quarter-circles. Suitably, respectively two adjacent, radially extending mixing elements are connected to each other in the above described manner while arranged at a circumferential displacement from one radial plane to the next.

In addition to the effect of the above described rigid mixing elements, it is of advantage for the mixing process if the mixer shaft is further provided with flexible scraper elements which, because of their flexibility or at least due to their flexible free ends arranged at a distance from the axis, will sweep along the inner wall of the tubular housing. Alternatively, the scraper elements can also be rigid and extend tangentially from the axis of the mixer haft. In the latter case, the two different radial planes of the mixer shaft have assigned thereto respectively two quasi diametrically opposite rigid scraper elements. Finally, it is also possible to provide flexible and rigid scraper elements together on the mixer shaft.

According to a further advantageous embodiment of the invention, it is provided that the mixer elements of the first radial planes which in the radial direction are adjacent to the inlet openings of the tubular portion of the housing, are shorter than the mixer elements in the other, second radial planes. Thus, the distance between the radially outer ends of the mixing elements and the tubular housing portion is larger in the first radial planes than in the second radial planes. This results in a larger mixer chamber in that region of the housing portion which joins the inlet openings. This enlarged mixer chamber offers the advantage that the dosage tolerances caused by the press-out or discharge device can be compensated for to a larger extent. By the additional arrangement of the tangentially projecting scraper elements within this enlarged mixer chamber, the respective leading material component has a longer dwelling time in the mixer chamber so that a longer time period will be available for mixing the slower material component to the leading material component.

However, a larger mixing chamber in the above described region is advantageously realized by lending the axis of the mixer shaft a smaller diameter than in the other region, and in that the mixing elements radially extend as far as all of the other mixing elements, notably up to the vicinity of the inner side of the tubular housing portion.

BRIEF DESCRIPTION OF THE DRAWINGS

An embodiment of the invention will be discussed hereunder in greater detail with reference to the accompanying drawings.

DETAILED DESCRIPTION OF PREFERRED EMBODIMENTS

Figure 1:
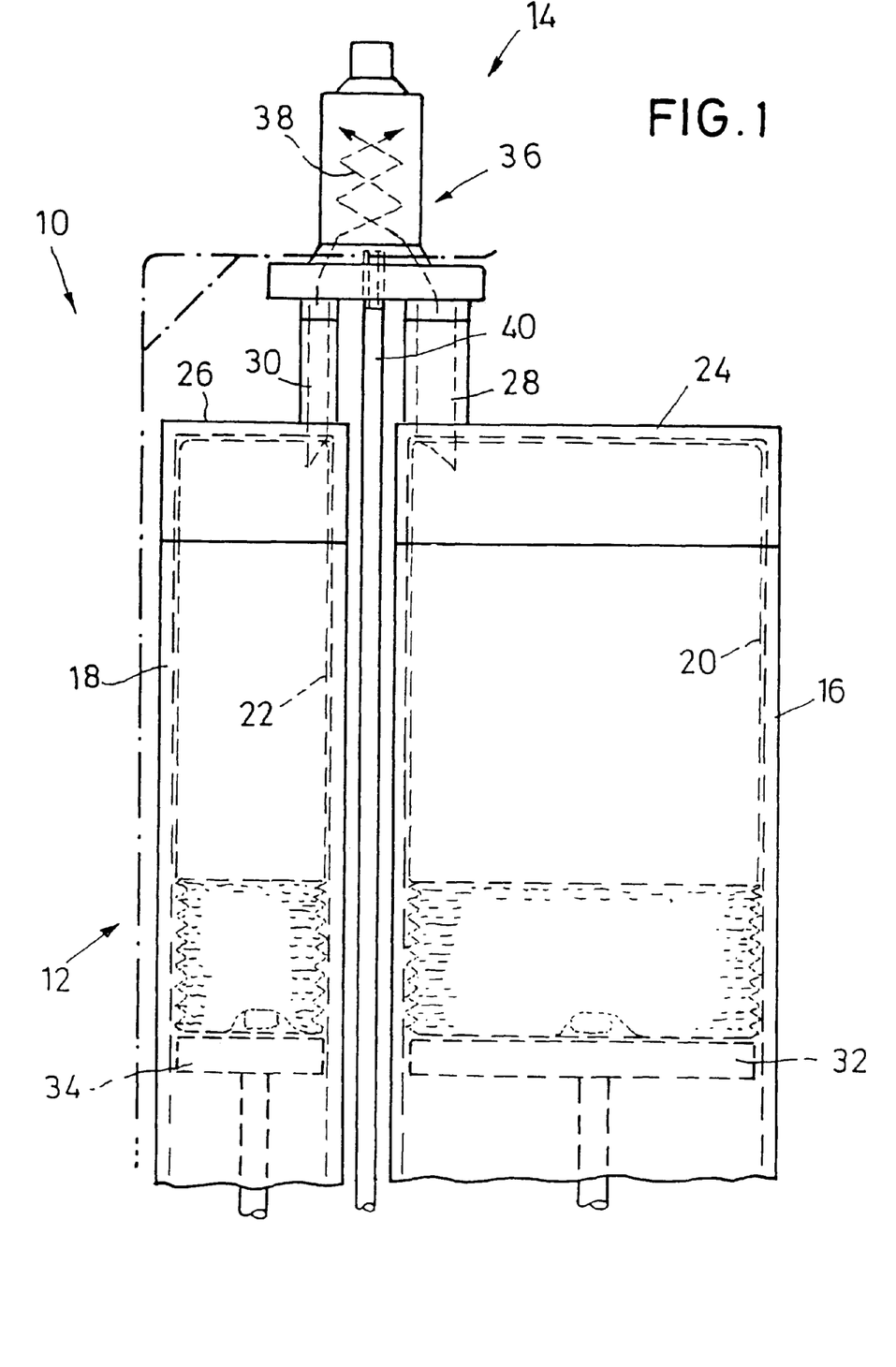
FIG. 1 is a general view of a dispensing device for mixed pasty components.

FIG. 1 shows a lateral general view of a dispensing device 10 for two pasty components to be mixed with each other.

Device 10 comprises a press-out member 12 and a mixing member 14, the press-out member 12 comprising two pressure containers 16,18 designed to accommodate two hose bags 20,22 containing the pasty substances. Pressure containers 16,18 have their front ends 24,26 provided with outlet connectors 28,30 defining outlet openings. Upon application of pressure onto the rear end of the hose bags 20,22, the content of the bags will be discharged via said outlet connectors 28,30. Pressurization of the hose bags 20,22 is performed by means of pressure stamps 32,34 driven by motors (not shown).

Outlet connectors 28,30 have a dynamic mixer 36 mounted thereon which shall still be described in greater detail with reference to FIGS. 2 to 7. It is a general feature of this dynamic mixer 36 that its mixer shaft 28 is motor-driven. For this purpose, mixer shaft 38 is arranged to be coupled to a drive rod 40 which is rotated by a motor (not shown).

Figure 2:
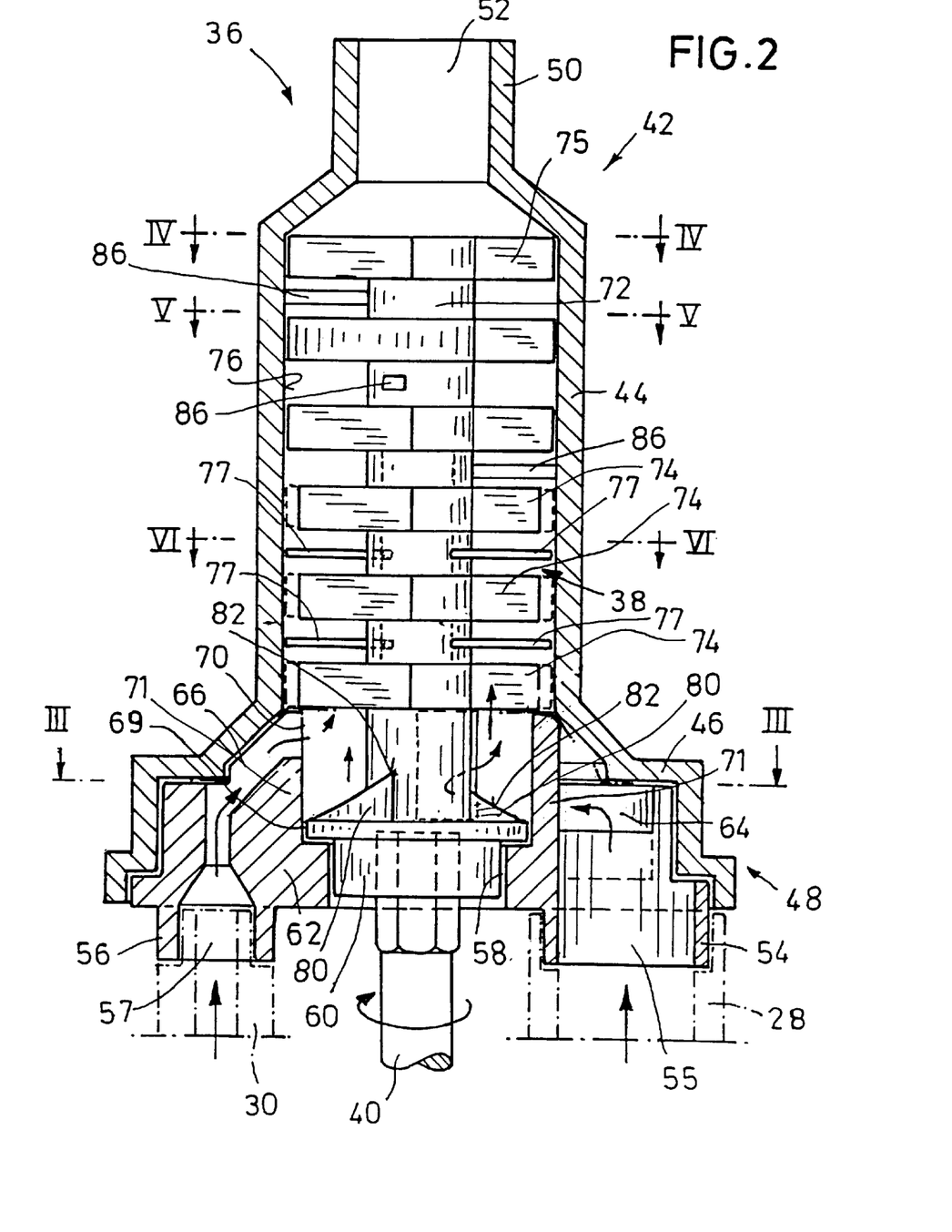
FIG. 2 is a longitudinal sectional view of the dynamic mixer used in the dispensing device according to FIG. 1.

The details of the dynamic mixer 36 are evident particularly from FIG. 2, showing a longitudinal sectional view of mixer 36. Mixer 36 has a housing 42 comprising a substantially cylindrical or tubular portion 44 with a conically widened coupling portion 46 arranged on the rear end 48 facing the press-out member 12, and a tapered front end 50. The tapered front end 50 is designed as an outlet stud and defines the outlet opening 52 for the material mixture, while the rear end 48 of housing 42 is provided with two inlet connectors 54,56 defining coupling openings 55 and 57 and provided to be mounted on the outlet connectors 28,30 of press-out member 12. Arranged between the two inlet connectors 54 is a perforation 58 for rotatable support of one end 60 of mixer shaft 38. Via this perforation, drive rod 40 can be coupled to mixer shaft 38.

The inlet connectors 54,56 and the perforation 58 are formed in an insert member 62 which on the rear end 48 of housing 42 is inserted into the conical coupling portion 46 of the housing. From the inlet connectors 54,56, two channels 64,66 extend through insert member 62, being deflected to enter radial openings 68,70. These inlet openings 68,70 are arranged radially with respect to the cylindrical portion 44 of mixer housing 42. The two pasty components are transported via channels 64,66 into the dynamic mixer 36 where they will then impinge onto the mixer shaft 38 in radial direction.

Figure 3:
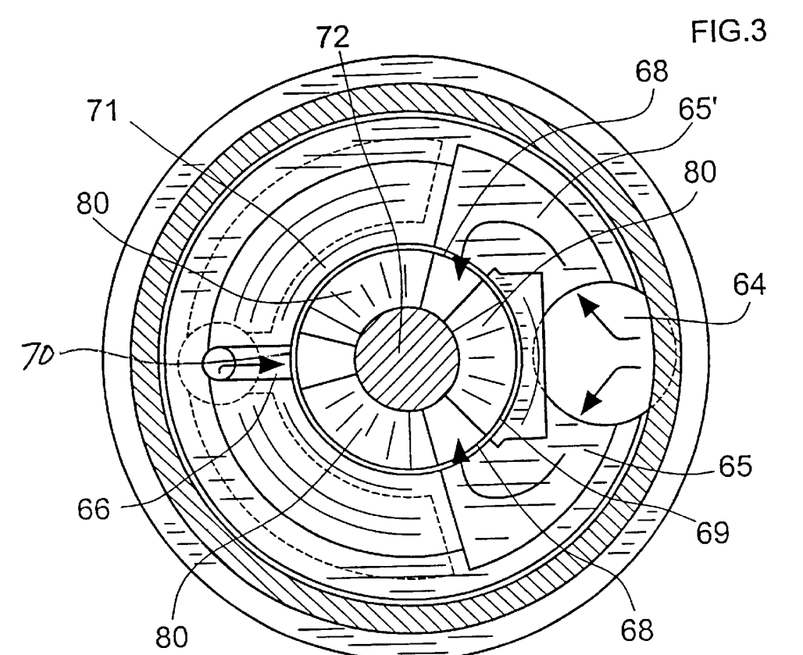
FIGS. 3 to 6 are cross-sectional views of the mixer according to FIG. 2, taken along the lines III—III, IV—IV, V—V and VI—VI in FIG. 2.

As evident from FIGS. 2 and 3, the insert member 62 comprises a centrally arranged, substantially cylindrical receiving recess 69 which is positioned concentrically to the perforation 58 and has the mixer shaft 38 inserted therein. The cylindrical wall 71 of the receiving recess 69 is formed with inlet openings 68,70. Further, also the channels 64,66 are provided in this region. These channels 64,66 are shaped as open-topped grooves or cutouts which together with the substantially conically widened coupling portion 46 form the channels which are closed on all sides.

As evident particularly from FIG. 3, channel 64 is divided into two partial channels 65,65'. These partial channels 65,65' extend from coupling opening 55 by substantially 60° circumferentially around the cylindrical wall 71 in opposite circumferential directions and terminate in separate inlet openings 68 arranged at a displacement of substantially 120°. Via these partial channels 65,65', the pasty substance with the higher throughput enters the mixer chamber. This substance will be the basic impression substance whose quantity, depending on the chemical composition, is about five times as large as the quantity of the catalyst substance entering the mixer chamber via channel 66 and via inlet opening 70. By introducing the substance with the larger volume into the mixer chamber at different sites along the circumference of the mixer chamber, the mixing between this substance and the other substance, i.e. the one with a smaller volume, is improved.

The configuration of the inventive mixer to the effect that one or both of the coupling openings 55,57 have a plurality of channels extending therefrom and terminating in a plurality of inlet openings 68,70 which, particularly in uniform distribution, enter the portion of the mixer housing 42 comprising the mixer shaft 38, does not only offer the advantage of an improved flow behavior of the pasty substances but primarily also the advantage of a better and more homogeneous mixing of the substances introduced into the mixer chamber. This effect is supported by the spatially distributed introduction of each of the two substances or at least one of the two substances. Notably, this distributed introduction of both substances or at least one of the two substances into the mixer chamber has the advantage of allowing for a kind of pre-mixing by the distribution of the substance flows among a plurality of inlet openings.

The individual partial channels can have the same lengths or different lengths. They can be provided as a collective channel originating from the respective coupling opening 55,57 and leading into a plurality of branch channels entering the inlet openings 68,70.

The mixer shaft 38 comprises a rotatably supported axis 72, wherein, in a plurality of radial planes, respectively four web-shaped mixing elements 74,75 are arranged to project from said axis substantially radially. The detailed arrangement of these mixer elements 74,75 is evident from the sectional view of FIG. 4. It can be seen that, of the two substantially radially extending limiting side edges 75 of the mixer elements 74, respectively one side edge extends substantially tangentially relative to the circumferential surface of axis 72. Further, it is evident that the first mixing elements 74 in the flow direction are shorter than the mixing elements 75 facing towards coupling opening 52. In other words, the radial distance of the mixing elements 74 to the inner surface 76 of the tubular housing portion 44 is larger than the comparable distance of the mixing elements 75. Thus, when viewed in the flow direction of the substances, the inlet openings 68,70 are followed by a mixer chamber portion within the tubular housing portion 44 which is larger than the mixer chamber portion having the longer mixing elements 75 assigned thereto. Further, between adjacent radial planes of mixing elements 74, tangentially projecting scraper elements 77 are arranged for improving the mixing effect. The first, larger-volumed portion of the mixer chamber further provides for a longer dwelling time of the above-mentioned one of the materials which is possibly leading also within the mixer chamber, so that the other material, flowing at a lower speed, will still have enough time for mixing with the first material.

In FIG. 2, interrupted lines schematically indicate a variant of the mixer wherein the axis 72 in the region of the first radial planes is thinner than within the other radial planes. In this arrangement, all of the mixing elements 74,75 have the same extension, i.e. up to the close vicinity of the tubular housing portion 44.

Figure 4:
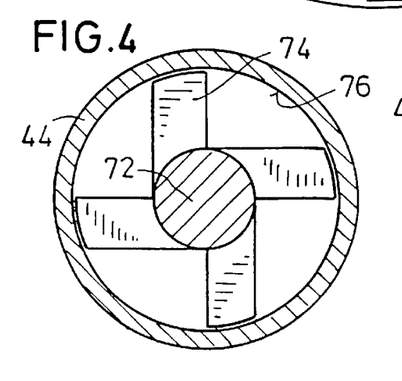
Figure 5:
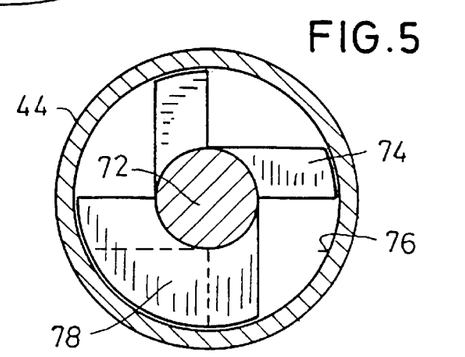

Thus, as illustrated in FIG. 4, respectively four mixing elements 74 are provided per radial plane, extending to positions close to the inner surface 76 of cylindrical housing portion 44. The whole area between the inlet openings 68,70 and the end of the mixer shaft 38 extending to the tapered end 50 of mixer housing 42, is provided with these mixing elements 74. Further, the mixer shaft 38 comprises mixing elements 78 configured as quarter-circle faces, which are formed by connecting respectively two adjacent mixing elements 74 in a radial plane (see e.g. the sectional view of FIG. 5). In this arrangement, the radially outer limiting edge of the mixing elements 78 is formed in the manner of a circular arc, while, in the alternative according to FIG. 7, this edge extends as a secant. Thus, the mixing element 78' of FIG. 7 in a central circumferential portion thereof has a larger distance to the inner surface 76 of the cylindrical housing portion 44.

While the mixing elements 74,78,78', due to their radial extension to the close vicinity of the cylindrical housing portion 44, will upon rotation of mixer shaft 38 provide for a deflection and thus a turbulence of the originally axially pasty substances, the mixer shaft 38 in the region of the radial inlet openings 68,70 comprises three baffle/deflection elements 80 formed in the manner of a worm conveyer. The baffle/deflection elements 80 are configured as saw-tooth-shaped wedges respectively extending by about 60° around the axis 72 of mixer shaft 38. The baffle/deflection elements 80 comprise a circumferentially ascending deflection face 82 facing towards the outlet opening 52 of the dynamic mixer 36 and arranged at an angular orientation to a plane extending radially to axis 72. These baffle/deflection elements 80 thus extend partially in a helical configuration and generate an axial motional component of the flows of pasty substances. Thus, the baffle/deflection elements 80 enhance the discharge of pasty substance entering the cylindrical housing portion 44 from the inlet openings 68,70. This supporting and thus intensifying removal effect acting on the pasty substances in the axial direction reduces the danger of contamination of the two pasty substances, i.e. an undesired mixing or backward contamination of the two pasty substances spreading via the inlet openings 68,70 into the channels 64,66 and possibly farther until reaching the outlet connectors 28,30. Notably, if a contamination and thus polymerization were to occur in these regions, the resulting clogging of the outlet connectors 28,30 would make it impossible to remove the rest of the material possibly remaining in the hose bags 20,22. Because of the regular arrangement of the baffle/deflection elements 80 and the inlet openings 68,70, the baffle/deflection elements 80 will also in case of exposed inlet openings always prevent a direct connection between adjacent inlet openings 68,70 (cf. FIG. 3). Also this baffle effect of the baffle/deflection elements 80 considerably contributes to the reducing of the danger of backward contamination since the catalyst substance issued e.g. from the inlet opening 70 cannot directly reach any of the inlet openings 68 for the basic impression substance, and vice versa.

Additionally to the baffle/deflection elements 80, the mixer shaft 38 can also comprise scraper bars arranged at radial distances from the axis 72 of mixer shaft 38 and in parallel to axis 72. Upon rotation of mixer shaft 38, the scraper bars are moved at a small distance internally along the cylindrical wall 71 of the insert member 62 and thus contribute to a generally more homogeneous mixing of the two substance flows.

Figure 6:
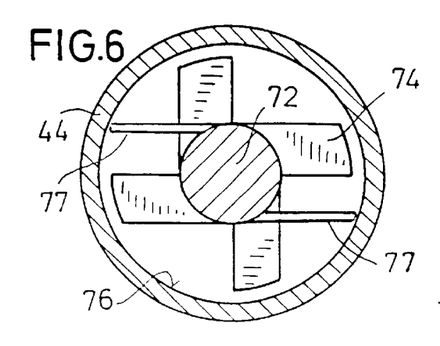
Figure 7:
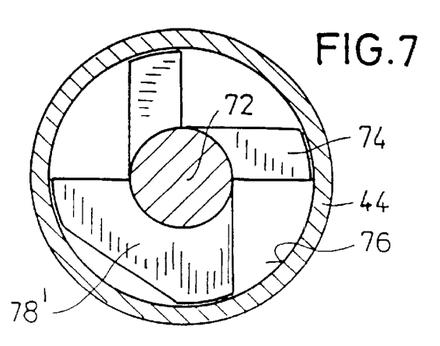
FIG. 7 is a cross-sectional view similar to FIG. 6, showing an alternative embodiment of the mixer shaft.

Referring now to FIG. 6, a further feature of the dynamic mixer will be explained hereunder. The mixing elements 74 discussed above are provided as rigid, radially projecting bars which, due to the rotation of axis 72, cause a turbulence of the substance flows. The dynamic mixer 36 can be provided, in addition to the rigid mixing elements 74,75 and the scraper elements 77, with further mixing elements 86 formed as thin flexible bars and sweeping internally along the inner surface 76 of the cylindrical housing portion 44. Also these additional mixing elements 86 are effective to cause a turbulence of the substance flows. Of the flexible mixing elements 86, respectively one exists in each of the plurality of successive radial planes of mixer shaft 38, and the mixing elements 86 are arranged at a constant angular displacement from one radial plane to the next. The same holds true for the mixing elements 78 and 78', respectively, which are arranged to connect to adjacent mixing elements 74,75 to each other and again are arranged at a displacement from one radial plane to the next, in this case by 90°. Thus, the mixing elements 86 and the mixing elements 78 or 78' are arranged along a helical line around axis 72 with uniform distribution. Both types of mixing elements are optimally suited for a homogeneous mixing of the pasty substances in the dynamic mixer 36 which also could be referred to as a flow-type mixer.

What is claimed is:

1. A device for mixing two pasty substances comprising a housing (42) including a substantially tubular portion (44) and at least two inlet openings (68, 70) for two pasty substances at a rear end of said housing (42), an outlet opening (52) for the mixed pasty substances at a front end of said housing (42), said housing (42) being provided with a coupling portion (46) having two coupling openings (55, 57) formed therein for connecting the housing (42) with two outlet openings (28, 30) of a device (12) for dispensing the two pasty substances, said coupling openings (55, 57) being connected to said at least two inlet openings (68, 70) through a respective first channel (64) and a second channel (66) each extending through said coupling portion (46), at least one mixer element (74, 75) arranged within said tubular portion (44) of said housing (12) for mixing the two pasty substances when the substances are passing through the tubular portion (44) of the housing (42), one of said first channel (64) and said second channel (66) extending through at least one of said at least two inlet openings (68, 70), said at least two inlet openings (68, 70) being spatially separated from each other, said first channel (64) being separated from said second channel (66), baffle elements (80) being arranged between said at least two inlet openings (68, 70) within the housing (42) for interrupting direct connection between said at least two inlet openings (68, 70), and the number and the relative arrangement of said baffle elements (80) being equal to the number and the relative arrangement of said at least two inlet openings (68, 70).

2. A device for mixing two pasty substances comprising a housing (42) including a substantially tubular portion (44) and at least two inlet openings (68, 70) for two pasty substances at a rear end of said housing (42), an outlet opening (52) for the mixed pasty substances at a front end of said housing (42), said housing (42) being provided with a coupling portion (46) having two coupling openings (55, 57) formed therein for connecting the housing (42) with two outlet openings (28, 30) of a device (12) for dispensing the two pasty substances, said coupling openings (55, 57) being connected to said at least two inlet openings (68, 70) through a respective first channel (64) and a second channel (66) each extending through said coupling portion (46), at least one mixer element (74, 75) arranged within said tubular portion (44) of said housing (12) for mixing the two pasty substances when the substances are passing through the tubular portion (44) of the housing (42), one of said first channel (64) and said second channel (66) extending through at least one of said at least two inlet openings (68, 70), said at least two inlet openings (68, 70) being spatially separated from each other, said first channel (64) being separated from said second channel (66), baffle elements (80) being arranged between said at least two inlet openings (68, 70) within the housing (42) for interrupting direct connection between said at least two inlet openings (68, 70), said at least one mixer element (74, 75) projecting radially from a mixer shaft (38) extending through said tubular portion (44) of the housing (42) and being supported for rotation therein, and said baffle elements (80) at said at least two inlet openings (68, 70) extending radially from said mixer shaft (38) and being arranged to sweep at least partially across said at least two inlet openings (68, 70) upon rotation of the mixer shaft (38).

3. The device as defined in claim 2 wherein each baffle element (80) includes a deflection face (82) extending around said mixer shaft (38) and being oriented obliquely relative to a radial plane of the mixer shaft (38) thereby to deflect the pasty substances radially entering said tubular portion (44) in an axial direction toward the outlet opening (52) of the housing (42).

4. The device as defined in claim 3 wherein each baffle element (80) is wedge-shaped.

5. The device as defined in claim 2 wherein the circumferential extension of the baffle elements (80) is equal to the circumferential distance between the at least two inlet openings (68, 70).

6. A device for mixing two pasty substances comprising a housing (42) including a substantially tubular portion (44) and at least two inlet openings (68, 70) for two pasty substances at a rear end of said housing (42), an outlet opening (52) for the mixed pasty substances at a front end of said housing (42), said housing (42) being provided with a coupling portion (46) having two coupling openings (55, 57) formed therein for connecting the housing (42) with two outlet openings (28, 30) of a device (12) for dispensing the two pasty substances, said coupling openings (55, 57) being connected to said at least two inlet openings (68, 70) through a respective first channel (64) and a second channel (66) each extending through said coupling portion (46), mixer elements (74, 75) arranged within said tubular portion (44) of said housing (12) for mixing the two pasty substances when the substances are passing through the tubular portion (44) of the housing (42), one of said first channel (64) and said second channel (66) extending through at least one of said at least two inlet openings (68, 70), said at least two inlet openings (68, 70) being spatially separated from each other, said first channel (64) being separated from said second channel (66), at least one of said mixer elements (74, 75) projects radially from an axis (72) of a mixer shaft (38) of said mixer elements (74, 75) toward an interface (76) of said tubular portion (44) of said housing (42), mixer elements (74) of first radial planes adjacent to each other in the radial direction to the at least two inlet openings (68, 70) are shorter than mixer elements (75) in other radial planes, and scraper elements (77) extend tangentially from the axis (72) of the mixer shaft (38) in association with at least one of said mixer elements (74, 75).

* * * * *